United States Patent
Becker et al.

(10) Patent No.: US 6,410,789 B1
(45) Date of Patent: Jun. 25, 2002

(54) PROCESS FOR PREPARING AROMATIC POLYAMINE MIXTURES

(75) Inventors: Rainer Becker, Bad Dürkheim; Karsten Eller, Ludwigshafen; Hans-Werner Langensiepen, Bobenheim-Roxheim; Michael Hesse, Worms, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/367,971

(22) PCT Filed: Feb. 20, 1998

(86) PCT No.: PCT/EP98/00981

§ 371 (c)(1),
(2), (4) Date: Nov. 8, 1999

(87) PCT Pub. No.: WO98/37124

PCT Pub. Date: Aug. 27, 1998

(30) Foreign Application Priority Data

Feb. 24, 1997 (DE) .......................... 197 07 255
Jun. 9, 1997 (DE) .......................... 197 24 237
Jun. 9, 1997 (DE) .......................... 197 24 213

(51) Int. Cl.⁷ ............................. C07C 211/00
(52) U.S. Cl. .................. 564/330; 564/332; 564/333
(58) Field of Search ................. 564/332, 330, 564/334, 333

(56) References Cited

U.S. PATENT DOCUMENTS

| | | | |
|---|---|---|---|
| 3,362,979 A | 1/1968 | Bentley | 260/453 |
| 4,039,580 A | 8/1977 | Frulla et al. | 260/570 |
| 4,039,581 A | 8/1977 | Frulla et al. | 260/570 |
| 4,071,558 A | 1/1978 | Bentley | 260/570 |
| 4,286,107 A | 8/1981 | Marquis et al. | 564/332 |
| 4,294,987 A | 10/1981 | Prather et al. | 564/331 |
| 5,371,246 A | * 12/1994 | Borchers et al. | |

FOREIGN PATENT DOCUMENTS

| | | |
|---|---|---|
| DE | 1230033 | 11/1963 |
| DE | 1493431 | 2/1969 |
| EP | 109931 | 5/1984 |
| EP | 264744 | 4/1988 |
| GB | 1207377 | 9/1970 |
| GB | 2066809 | 7/1981 |

* cited by examiner

Primary Examiner—Samuel Barts
(74) Attorney, Agent, or Firm—Keil & Weinkauf

(57) ABSTRACT

In a process for preparing aromatic polyamine mixtures which contain compounds of the formula (I), $$H_2N-A-CH_2-B-NH_2 \qquad (I)$$

where A and B are 1,4-phenylene radicals each of which independently of one another can have 1 to 4 substituents selected from $C_{1-20}$ alkyls and halogens,
a compound of the formula (IV)

$$H-A-NH-CH_2-HN-B-H \qquad (IV)$$

and/or a compound of the formula (V)

$$H-A-NH-CH_2-B-NH_2 \qquad (V)$$

where A and B are substituted as above,
are reacted at from 20° C. to 200° C. in the presence of a heterogeneous inorganic catalyst selected from the group consisting of a) one or more oxides of elements of group 3 to group 10 of the Periodic Table of the Elements, which can be acid-activated, b) a clay which is doped with at least one oxide of elements of groups 2 to 13 or the lanthanides of the Periodic Table of the Elements and can be acid-activated or c) a catalyst comprising one or more sheet silicates which may be acid-activated and have an acidity below $pK_a=$ 1.5 of more than 0.05 mmol/g of catalyst.

17 Claims, No Drawings

PROCESS FOR PREPARING AROMATIC POLYAMINE MIXTURES

This application is a 371 of PCT/EP98/00981 filed Feb. 20, 1998.

The invention relates to a process for preparing aromatic polyamine mixtures from unsubstituted or substituted aniline and formaldehyde or formaldehyde precursors or a condensation product of these compounds.

Unsubstituted or substituted diaminodiarylmethanes are valuable precursors particularly for the preparation of plastics. The unsubstituted diaminodiphenylmethane (frequently called methylenedianiline, MDA), especially, is produced industrially in very great amounts and the majority, after phosgenation to give methylenediphenyl diisocyanate (MDI), is used for the preparation of polyurethanes. Preferably, the 4,4' isomer is used for this, but the 2,4' and 2,2' isomers are also produced in the known preparation processes. In addition, more highly condensed polynuclear compounds are formed. They are generally prepared from aniline and formaldehyde in the presence of catalysts.

In the industrially used processes, inorganic acids in dissolved form are used as homogeneous catalysts. Preferably, aqueous hydrochloric acid is used. This reaction procedure leads, owing to the work-up, to the consumption of equimolar amounts of bases, since the acids still need to be neutralized during the isolation of the desired polyamines. This process is therefore inevitably associated with a production of correspondingly high amounts of salt which must be disposed of or recirculated by complicated means. In addition, the corrosion problems associated with the use of aqueous acids are a considerable disadvantage of this process.

For this reason, great consideration has been given to, and there have been numerous attempts at replacing aqueous homogeneous catalysts by acid heterogeneous catalysts. In addition to acid ion exchangers, the use of acidic synthetic or natural silicon oxides or aluminum oxides, such as zeolites or clay minerals, has been proposed. DE-A-1 230 033, DE-A-1 493 431, U.S. Pat. Nos. 4,071,558, 4,039,580, 4,039,581, and 4,294,987 describe corresponding catalysts.

According to U.S. Pat. No. 4,294,981, in a process of this type, the condensation is carried out in the presence of a strong aqueous acid, after which the acid is removed by solvent extraction. The rearrangement is in turn carried out in the presence of strong acid which is used in a smaller amount. Diatomaceous earth, clay or zeolites can be used in this stage.

According to DE-A-1 230 033, siliceous clay, a synthetic silicon dioxide-aluminum oxide catalyst or a magnesium oxide-aluminum oxide catalyst is used.

According to DE-A-1 493 431, silicon dioxide, silicon dioxide/aluminum oxide or acid-treated aluminum oxide is used as catalyst. Preferably, silica gel or bentonite-like clay, which contains silicon dioxide and aluminum oxide and is preferably acid-activated, is used. However, considerable amounts of higher condensation products are formed in addition to the desired diaminodiarylmethanes.

According to U.S. Pat. No. 4,071,558, an acid-activated clay catalyst, a silicon dioxide-aluminum oxide cracking catalyst or a silicon dioxide-magnesium oxide catalyst is used. Here too, relatively large amounts of 2,4' isomers and higher molecular weight products are formed when using the clay catalyst.

According to U.S. Pat. Nos. 4,039,580, 4,039,581 and 4,294,987, a mixture of diaminodiarylmethanes and more highly condensed oligomers is obtained in a complicated two-stage process. Apart from aqueous acids, use is also made of diatomaceous earth, clays or zeolites.

According to U.S. Pat. No. 4,294,987, the condensation is carried out in the presence of a strong aqueous acid, after which the acid is removed by solvent extraction. The rearrangement is again carried out in the presence of strong acid which is used in a smaller amount. Diatomaceous earth, clays or zeolites can also be used in this stage.

According to U.S. Pat. No. 4,039,580, a condensation of aniline and formaldehyde is carried out in the absence of a catalyst and the condensation product is reacted in the presence of diatomaceous earth, clays or zeolites. The diamine content of the product is from 44 to 50%. U.S. Pat. No. 4,039,581 describes similar reactions. However, owing to their high prices, their insufficient activities or unsatisfactory catalyst operating lives, these catalysts have not been able to become established in the industry. High proportions of 4,4' isomers and very low contents of more highly condensed products cannot be obtained in these processes. Relatively large proportions of 2,4' or 2,2' isomers are always obtained.

For this reason, there continues to be a demand for heterogeneous catalysts which are inexpensive, have a high activity and a long operating life, are environmentally compatible and lead to high yields of 4,4' isomers with small amounts of more highly condensed products.

It is an object of the present invention to provide catalysts which have the abovementioned properties, and to provide a process for preparing aromatic polyamine mixtures.

We have found that this object is achieved by a process for preparing aromatic polyamine mixtures which contain compounds of the formula (I)

$$H_2N-A-CH_2-B-NH_2 \quad \text{(I)}$$

where A and B are 1,4-phenylene radicals each of which independently of one another can have from 1 to 4 substituents selected from $C_{1-20}$ alkyls and halogens, by reacting a compound of the formula (IV)

$$H-A-NH-CH_2-HN-B-H \quad \text{(IV)}$$

and/or a compound of the formula (V)

$$H-A-NH-CH_2-B-NH_2 \quad \text{(V)}$$

where A and B are substituted as above,
at from 20° C. to 200° C. in the presence of a heterogeneous inorganic catalyst selected from the group consisting of
  a) one or more oxides of elements of group 3 to group 10, preferably group 4 to group 6, of the Periodic Table of the Elements, which can be acid-activated,
  b) a catalyst comprising a clay which is doped with at least one oxide of elements of groups 2 to 13 or the lanthanides of the Periodic Table of the Elements and can be acid-activated or
  c) a catalyst comprising one or more sheet silicates which may be acid-activated and have an acidity below $pK_a$= 1.5 of more than 0.05 mmol/g of catalyst.

In this process, the compound of the formulae (IV) and/or (V) can be obtained by reacting aniline, which is unsubstituted or substituted at the aromatic ring in the o- or m-position with from 1 to 4 substituents selected from $C_{1-20}$ alkyls or halogens, with formaldehyde or formaldehyde precursors.

In addition, the object is achieved by a process for preparing aromatic polyamine mixtures which contain compounds of the formula (I)

where A and B are 1,4-phenylene radicals each of which independently of one another can have from 1 to 4 substituents selected from $C_{1-20}$ alkyls and halogens, by reacting anilines, which are unsubstituted or substituted at the aromatic ring in the o- or m-position with from 1 to 4 substituents selected from $C_{1-20}$ alkyls and halogens, with formaldehyde or formaldehyde precursors at from 20° C. to 200° C. in the presence of a heterogeneous catalyst selected from the group consisting of a) one or more oxides of elements of group 3 to group 10, preferably group 4 to group 6, of the Periodic Table of the Elements, which can be acid-activated, b) a catalyst comprising a clay which is doped with at least one oxide of elements of groups 2 to 13 or the lanthanides of the Periodic Table of the Elements and can be acid-activated, or c) a catalyst comprising one or more sheet silicates which may be acid-activated and have an acidity below $pK_a = 1.5$ of more than 0.05 mmol/g of catalyst.

Catalyst a)

It has been found according to the invention that oxides of elements of group 3 to group 10, preferably group 4 to group 6 of the Periodic Table of the Elements or their mixtures may be used highly advantageously as catalysts in the abovementioned reactions. The division into groups of the Periodic Table is in accordance with the new notation, see Cotton and Wilkinson, Advanced Inorganic Chemistry, 5th edition, John Wiley & Sons.

Preferably, oxides of group 4 and/or group 6 of the Periodic Table of the Elements are used. Particularly preferably, as catalyst, use is made of titanium dioxide, tungsten oxide, molybdenum oxide, zirconium dioxide or mixtures of these. For the purposes of the invention, "mixtures" are mixtures of two or more of the abovementioned oxides. They may be mixtures of the individual pulverulent oxides, or joint precipitation products from solutions which contain the soluble compounds of the metals. Processes for preparing the catalysts used according to the invention are known.

The abovementioned catalysts can also be acid-activated. Acid activation may be performed, for example, by sulfuric acid, phosphoric acid or hydrochloric acid, preferably by sulfuric acid. The catalysts can thus contain sulfate, phosphate or chloride.

The abovementioned catalysts can preferably contain sulfate. For this purpose, for example, the oxide catalyst is soaked in sulfuric acid and then dried. By this means the catalysts become sulfate-containing catalysts. The content of acid, preferably sulfate or sulfuric acid can vary within broad ranges and can easily be adapted to the desired conditions. The catalyst can also be prepared by soaking in acid-containing, preferably sulfate-containing solutions, such as alkali metal salt solutions or alkaline earth metal salt solutions, and then drying.

Catalyst b)

The group classification of the Periodic Table follows the new notation, cf Cotton and Wilkinson, Advanced Inorganic Chemistry, 5th Edition, John Wiley & Sons.

As clays for the catalysts, it is possible to use all dioctahedral or trioctahedral representatives, for example kaolin, talc, pyrophylite, smectites such as hectorite or montmorillonite, vermiculite, sepiolite or attapulgite. Preference is given to saponite, hectorite, montmorillonite, sepiolite and attapulgite; particular preference is given to montmorillonite. These clays can either be of natural origin or be synthetic.

The clays can be doped either in their naturally occurring form or after a prior acid activation. Depending on the treatment, if any, the clays prior to doping thus contain different amounts of alkali metal and alkaline earth metal ions as well as the impurities such as iron ions always present in natural clays. The acid activation can be carried out using various acids; preference is given to the customary mineral acids such as hydrochloric acid, sulfuric acid or phosphoric acid. Particular preference is given to hydrochloric acid. Acid-activated sheet silicates are commercially available under the names bleaching earths or Fuller's earth.

The oxides of groups 2 to 13 or the lanthanides can be applied to the clays by the customary methods. For example, the dried clay can be admixed with a solution of the metals to be applied in the form of their nitrates or acetates in an amount calculated such that the amount of liquid absorbed contains exactly the desired amount of the metal nitrates or acetates. Drying and calcination converts the nitrates or acetates into the desired oxides. Other salts which can be used are, for example, oxalates or citrates, but it is in principle possible to use all soluble salts which are converted completely or partially into the desired oxides during the subsequent catalyst preparation steps. If the oxides themselves are soluble, they can also be used directly.

Instead of being carried out by impregnation as described above, the doping can also be carried out by means of ion exchange. For this purpose, the clay is placed as a powder in suspension or as shaped bodies in a circulation reactor and brought into contact with a solution which contains the metals to be applied in ionic form. The metal ions then replace part of the alkali metal, alkaline earth metal or hydrogen ions of the clay. The clay may then be washed and is again dried and possibly calcined. The ion exchange can be carried out using all soluble metal compounds which, after washing, drying or calcination, leave no impurities which have an adverse effect on the catalysis. They are usually chlorides, nitrates or acetates of the metals used according to the present invention.

The impregnated or doped sheet silicates are advantageously dried at atmospheric pressure and at 80–200° C., preferably 100–150° C., for from 1 to 20 hours. However, drying can also be carried out under reduced pressure and at lower temperatures. Calcination of the dried catalysts is carried out at 150–600° C., preferably 170–500° C., for from 0.5 to 12 hours, preferably from 1 to 5 hours.

The amount of oxide applied varies as a function of the oxide used or the oxide mixture used and of the amine employed. However, the optimum content can easily be determined empirically by means of a concentration series. According to the present invention, even very low contents of 0.1% by weight, calculated as metal oxide and based on the total weight of the catalyst, can have a positive catalytic effect. However, at very high contents of over 20% by weight, no further increase in the activity and selectivity will be possible. Preference is therefore given to contents of from 0.2 to 10% by weight, particularly preferably from 0.3 to 7% by weight. The content is given as percent by weight of the stabilizing oxide of the respective element for a sheet silicate ignited at 900° C., but, since the precise environment of the metal ions in the finished catalyst is not known in detail, it is also possible that the sheet silicate functions as counterion and/or that residues of the anion used for application of the metal still remain in the catalyst.

Among the oxides of groups 2 to 13 or the lanthanides, preference is given to the oxides of groups 2 to 4, 7, 13 or the lanthanides. Particular preference is given to oxides of barium or strontium from group 2, lanthanum oxide from group 3, hafnium oxide from group 4, rhenium oxide from group 7, indium oxide from group 13 and also the lanthanides.

Catalyst c)

It has been found according to the present invention that sufficiently high yields of the desired 4,4'-diaminodiarylmethanes are obtained only when using certain sheet silicates. In the case of sheet silicates which are not according to the present invention, the formation of the polyamine mixtures does occur but, firstly, is very much slower and, secondly, is associated with the dis-advantages indicated in the above-described patents, eg. a low 4,4'-selectivity and formation of more highly condensed compounds.

Catalysts which do not have these deficiencies are distinguished by an acidity of more than 0.05 mmol of butylamine per gram of catalyst in a titration against Hammett indicators, specifically the Hammett indicator 4-phenylazodiphenylamine ($pK_a$=1.5), as described in Tanabe et al., New Solid Acids and Bases, Stud. Surf. Sci. Catal. 51, 1989, Chapter 2, and Benesi, J. Phys. Chem. 61, 1957, pp. 970–973. To determine the acidity, the dried catalyst is suspended in an inert aprotic solvent such as toluene and the indicator having the defined $pK_a$ value of 1.5 plus n-butylamine or a similar base is added. Since the reaction of the solid acid with the base occurs slowly, the titration cannot be carried out in the customary manner by means of a burette, but increasing amounts of base are added in a plurality of batches, the mixtures are shaken over night, and on the next morning, after establishment of equilibrium, are checked to determine which amounts of base have caused a color change. A quantitative measure of acidity centres in mmol of base per gram of solid acid below the $pK_a$ of the indicator of 1.5 is thus obtained.

Possible sheet silicates for the catalysts are all dioctahedral or trioctahedral representatives, for example kaolin, talc, pyrophylite, smectites such as hectorite or montmorillonite, vermiculite, muscovite, sepiolite or attapulgite. Preference is given to saponite, hectorite, montmorillonite, sepiolite and attapulgite. Particular preference is given to montmorillonite, sepiolite and attapulgite. The clays can either be of natural origin or be synthetic. For the catalysis, it is immaterial whether a single defined sheet silicate or a mixture of various sheet silicates is employed. Particularly when using naturally occurring sheet silicates, various sheet silicates are frequently present simultaneously.

The sheet silicates can have a sufficient acidity below $pK_a$=1.5 either in their naturally occurring form or after a prior acid activation. They thus comprise different amounts of alkali metal and alkaline earth metal ions and also the impurities which are always present in natural clays, eg. iron ions. If an acid activation is necessary to achieve a sufficiently high acidity, this can be carried out using various acids. Preference is given to the customary mineral acids such as hydrochloric acid, sulfuric acid or phosphoric acid. Particular preference is given to hydrochloric acid. Acid-activated sheet silicates are available commercially under the names bleaching earths or Fuller's earths.

The catalysts can be pulverulent or in the form of shaped bodies, such as extrudates, granules, tablets, pellets or spheres. Correspondingly, the reaction can be carried out in suspension or using fixed-bed catalysts. The reaction can be carried out batchwise or continuously in all cases.

According to an embodiment of the process according to the invention, aniline, which is unsubstituted or substituted at the aromatic ring in the o- or m-position with from 1 to 4 substituents selected from $C_{1-20}$, preferably $C_{1-10}$, particularly preferably $C_{1-6}$ in particular $C_{1-3}$ alkyls and halogens, preferably fluorine, chlorine or bromine, in particular chlorine, is reacted with formaldehyde or formaldehyde precursors.

Preferably, in the unsubstituted or substituted aniline, from 0 to 2, particularly preferably no or one, substituent(s) is/are present. If one substituent is present, it is preferably an alkyl, in particular methyl, ethyl or propyl. This substituent is preferably in the o-position. Compounds which are preferably used are aniline or o-toluidine. The unsubstituted or substituted aniline is reacted with formaldehyde or formaldehyde precursors. As formaldehyde precursors, use is made of those compounds which release formaldehyde under the reaction conditions. Examples of these are paraformaldehyde and trioxane.

The reaction can be carried out directly in the presence of the catalyst according to the invention, i.e. the catalyst is added directly right at the beginning of the reaction. In this case, the unsubstituted or substituted aniline, for example, can be charged together with the catalyst and the formaldehyde can be added in the gaseous state or as aqueous solution or as formaldehyde precursor. The reaction can also be carried out by charging the formaldehyde or the formaldehyde precursor together with the unsubstituted or substituted aniline and then introducing the catalyst. According to this further embodiment of the invention, the formaldehyde is first reacted with the unsubstituted or substituted aniline in the absence of the catalyst, a condensation compound of the formula (IV) or (V) forming. This precondensate can then be reacted in the presence of the catalyst according to the invention, with the rearrangement to give a compound of the formula (I) occurring.

The reaction water produced during the formation of the precondensate can be removed continuously. It can alternatively be removed by distillation at the end of the reaction to form the precondensate or can remain in the reaction mixture.

If an unsubstituted or substituted aniline is used in which the o-positions are not both substituted, during the isomerization, in addition to the 4,4' isomers of the formula (I), the 2,4' isomers of the formula (II) and the 2,2' isomers of the formula (III) can also be formed. The invention thus also relates to a process in which the aromatic rings are unsubstituted at at least one opposition to the amino group and the aromatic polyamine mixtures in addition contain compounds of the formulae (II) and/or (III)

$$H_2N\text{—}D\text{—}CH_2\text{—}B\text{—}NH_2 \qquad (II)$$

where D is a 1,2-phenylene radical and B is a 1,4-phenylene radical, which may be substituted by the above substituents,

$$H_2N\text{—}D\text{—}CH_2\text{—}E\text{—}NH_2 \qquad (III)$$

where D and E are 1,2-phenylene radicals, which may be substituted by the above substituents.

By using the catalysts according to the invention, the proportion of the compounds of the formula (I) can be specifically varied with respect to the proportion of the compounds of the formulae (II) and (III). Compounds of the formula (III) are only formed to a very minor extent. The molar ratio of compounds of the formula (I) to compounds of the formula (II) is preferably greater than 4, provided that compounds of the formula (II) can be formed.

The reaction according to the invention, in particular the rearrangement reaction, preferably proceeds at from 20° C. to 200° C., particularly preferably from 100° C. to 150° C. The reaction can be carried out in the absence or presence of a solvent. As solvent, use is made of protic solvents such as alcohols, also diols such as glycol, or aprotic solvents such as N-methylpyrrolidone. Preferably, the reaction is carried out in the absence of a solvent.

The reaction is customarily carried out at atmospheric pressure, but can also be carried out at reduced pressure or at superatmospheric pressure. The reaction time, depending on temperature, is preferably from 10 minutes to 10 hours, particularly preferably from 0.2 to 5 hours or 1 to 5 hours with the batch procedure. The amount of catalyst used is from 1 to 40, preferably from 5 to 20, percent by weight for catalyst a) and 1 to 50, preferably 5 to 40, percent by weight, for catalysts b) and c), based on the weight of the precondensate. In the continuous procedure, a catalyst loading of from 0.1 to 1 l of starting mixture/l of catalyst×h is preferably employed. The molar ratio of the unsubstituted or substituted aniline to the formaldehyde is preferably from 2 to 50, particularly preferably from 2.5 to 10.

For the work-up, the reaction mixture, after filtering off the catalyst powder in the case of the suspension procedure, is freed by distillation from any solvent present, or any unreacted unsubstituted or substituted aniline, and is then distilled off from any high-boiling residue produced. The polyamine mixture obtained as distillate in this case can be used directly in subsequent reactions, such as a phosgenation or else ring hydrogenation.

The examples illustrate the invention.

Parts and percentages are by weight.

Catalyst a)

EXAMPLE 1

Batch Procedure 3210 parts of o-toluidine are mixed with 405 parts of 37% strength aqueous formaldehyde solution, the water is removed by azeotropic distillation and the remaining mixture ("precondensate") is admixed with 54 parts of commercial titanium dioxide powder (for example VKR611 from Sachtleben, Germany). After heating to 130° C., the rearrangement is complete after 30 minutes. The crude reaction mixture contains, in accordance with gas-chromatographic analysis, in addition to 68% of unreacted toluidine, 28.3% of the wanted diaryldiaminomethane as a mixture of isomers having a ratio of 4,4'-isomer to 2,4'-isomer of 10.5.

EXAMPLE 2–13

In these examples, a procedure similar to Example 1 is employed, but with different catalysts a) or under different conditions:

| Ex. No. | Catalyst a) | Temp. | Conversion after 120 min | Isomeric ratio* |
|---|---|---|---|---|
| 2 | $ZrO_2/WO_3$ (20%) | 130° C. | 100% | 13.9 |
| 3 | $TiO_2/WO_3$ (15%)[1] | 130° C. | 100% | 15.8 |
| 4 | $TiO_2/WO_3$ (15%)[2] | 130° C. | 100% | 9.7 |
| 5 | $ZrO_2$ | 130° C. | <10% | — |
| 6 | $WO_3$ | 130° C. | approx. 70% | — |
| 7 | $TiO_2/SO_4$ (2.4% S)[3] | 100° C. | approx. 70% | — |
| 8 | $TiO_2/SO_4$ (2.4% S) | 130° C. | 100% | 10.5 |
| 9 | $TiO_2/SO_4$ (2.4% S) | 170° C. | 100% | 4.8 |
| 10 | $TiO_2/WO_3$ (5%) | 130° C. | approx. 20% | — |
| 11 | $TiO_2/MoO_3$ (15%) | 130° C. | 100% | 9.4 |
| 12 | $ZrO_2/MoO_3$ (20%) | 130° C. | 100% | 17.2 |
| 13 | $ZrO_2/SO_4$ (3% S) | 130° C. | approx. 80% | — |

[1]heated at 650° C.
[2]heated at 250° C.
[3]% based on sulfur in the $SO_4$
*of the 4,4' to the 2,4'-isomers; the 2,2'-isomer is not detectable

EXAMPLE 14

Continuous Procedure 100 ml of $TiO_2$ are charged, as extrudate having a diameter of 2.5 mm, into the reactor of a continuous plant. Adduct (precondensate), which itself was prepared from 1600 g of o-toluidine, 203 g of aqueous formaldehyde solution (75 g of formaldehyde calculated as 100%) and 1600 g of ethylene glycol as solvent, is continuously pumped over the catalyst bed with a residence time of approximately 20 hours at 130° C.

The crude discharge has the following composition according to gas chromatography:

67.4% of o-toluidine 2.7% of 2,4'-toluidine base 29.9% of 4,4'-toluidine base (each calculated as glycol-free)

Catalyst b)

Catalyst preparation of Catalyst b) cl Catalyst A

Catalyst A was prepared from commercially available K 10 (acid-activated montmorillonite from Südchemie) which had been converted into extrudates beforehand. A solution of 100 g of $Ba(NO_3)_2$ in 2 liters of distilled water was pumped at 50° C. over 1200 g of the extrudates for 3 hours and the extrudates were then rinsed briefly with distilled water. After drying at 120° C. for 16 hours, the extrudates were calcined at 200° C. for 2 hours. Catalyst A contained 1.25% of BaO.

Catalyst B

Catalyst B was prepared by a method similar to catalyst A, except that a mixture of various nitrates of the rare earth was used in place of $Ba(NO_3)_2$. Catalyst B contained 2.7% of $CeO_2$, 1.48% of $La_2O_3$, 0.32% of $Pr_2O_3$ and 1.11% of $Nd_2O_3$.

Catalyst C

Catalyst C was prepared by a method similar to catalyst A, except that $Ga(NO_3)_3 \cdot 9H_2O$ was used in place of $Ba(NO_3)_2$ and calcination was carried out at 400° C. Catalyst C contained 1.13% of $Ga_2O_3$.

Catalyst D

Catalyst D was prepared by a method similar to catalyst A, except that $Sr(NO_3)_2$ was used in place of $Ba(NO_3)_2$ and calcination was carried out at 400° C. Catalyst D contained 0.84% of SrO.

Catalyst E

Catalyst E was prepared using a method similar to catalyst A, except that $In(NO_3) \cdot 5H_2O$ was used in place of $Ba(NO_3)_2$ and calcination was carried out at 400° C. Catalyst E contained 1.57% of $In_2O_3$.

Catalyst F

Catalyst F was prepared using a method similar to catalyst A, except that $HfCl_4$ was used in place of $Ba(NO_3)_2$ and calcination was carried out at 400° C. Catalyst F contained 3.3% of $HfO_2$.

Catalyst G

Catalyst G was prepared from commercially available K 10 (acid-activated montmorillonite from Südchemie) which had been converted into extrudates beforehand. A solution of 120 g of $Re_2O_7$ in 4 liters of distilled water was pumped at 50° C. over 2000 g of the extrudates for 3 hours and the extrudates were then rinsed briefly with distilled water. After drying at 120° C. for 16 hours, the extrudates were calcined at 400° C. for 2 hours. Catalyst G contained. 0.65% of $Re_2O_7$.

Catalyst H

Catalyst H was prepared from commercially available K 10 (acid-activated montmorillonite from Südchemie) which had been converted into extrudates beforehand. A solution of 400 g of $Re_2O_7$ in 3 liters of distilled water was pumped at 50° C. over 2000 g of the extrudates for 6 hours and the extrudates were then rinsed briefly with distilled water. After drying at 120° C. for 16 hours, the extrudates were calcined at 400° C. for 2 hours. Catalyst H contained 0.45% of $Re_2O_7$.

Reaction to Form Polyamines 160 g (1.5 mol) of o-toluidine were admixed at room temperature with 7.5 g (0.25 mol) of formaldehyde (as a 37% strength aqueous solution) and the water was subsequently removed at 150° C. by means of a water separator. The resulting solution of this precondensate in toluidine was used directly for the reaction with the catalysts b).

For this purpose, in each case 40% by weight (based on the adducts of formaldehyde and two molecules of toluidine) of catalyst b) was added in powder form and the mixture was heated while stirring to 100° C. The results obtained using the various catalysts after different reaction times are shown in Table 1. A content of about 30% of methyleneditoluidine here corresponds to the maximum possible yield. The isomer ratio indicated gives the proportion of the 4,4' isomer relative to the 2,4' isomer.

TABLE 1

| Catalyst b) | Running time (h) | Methyleneditoluidine [%] | Isomer ratio |
|---|---|---|---|
| A | 0.5 | 27.9 | 7 |
| A | 1 | 28.0 | 6.7 |
| A | 2 | 27.7 | 6.4 |
| B | 0.5 | 26.0 | 9.3 |
| B | 1 | 26.8 | 8.4 |
| B | 2 | 26.4 | 7.5 |
| C | 0.5 | 26.0 | 9.3 |
| C | 1 | 26.8 | 8.4 |
| C | 2 | 26.4 | 7.5 |
| D | 0.5 | 28.6 | 11.4 |
| D | 1 | 28.8 | 10.7 |
| D | 2 | 29.1 | 9.7 |
| E | 0.5 | 29.2 | 12.2 |
| E | 1 | 28.7 | 10.6 |
| E | 2 | 29.8 | 9.6 |
| F | 0.5 | 28.9 | 13.8 |
| F | 1 | 28.5 | 13.0 |
| F | 2 | 28.8 | 11.1 |
| G | 0.5 | 28.8 | 12.0 |
| G | 1 | 29.0 | 10.4 |
| G | 2 | 28.1 | 8.8 |
| H | 0.5 | 29.0 | 11.7 |
| H | 1 | 29.2 | 10.1 |
| H | 2 | 29.2 | 9.1 |

Catalyst c)
Catalyst Preparation of Catalyst c)

Catalyst A (Comparative Example)

Catalyst A was a commercially available acid-activated montmorillonite from Südchemie (Grade: KSF) without acid centers below $pK_a=1.5$.

Catalyst B

Catalyst B was a commercially available acid-activated montmorillonite from Südchemie (Grade: K 10) having an acidity of 0.061 mmol $g^{-1}$ below $pK_a=1.5$.

Catalyst C

Catalyst C was a commercially available attapulgite from Floridin.

Catalyst D (Comparative Example)

Catalyst D was obtained by acid activation (0.5 M $H_2SO_4$, 12 hours at 50° C.) of a commercially available sepiolite from Oxymine. It had no acidity below $pK_a=1.5$.

Catalyst E (Comparative Example)

Catalyst E was obtained by acid activation (1 M HCl, 24 hours at 50° C.) of a commercially available sepiolite from Sobrep. It had no acidity below $pK_a=1.5$.

Catalyst F

Catalyst F was obtained by acid activation (1 M HCl, 4 hours at 50° C.) of a commercially available montmorillonite (Terrana D from Südchemie). It had an acidity of 0.090 mmol $g^{-1}$ below $pK_a=1.5$.

Catalyst G (Comparative Example)

Catalyst G was obtained by acid activation (0.5 M $H_2SO_4$, 6 hours at 50° C.) of a commercially available synthetic hectorite (Laponit RD from Laporte). It had an acidity of 0.021 mmol $g^{-1}$ below $pK_a=1.5$.

Catalyst H

Catalyst H was obtained by acid activation (0.5 M $H_3PO_4$, 12 hours at 50° C.) of a commercially available montmorillonite (Terrana D from Südchemie). It had an acidity of 0.10 mmol $g^{-1}$ below $pK_a=1.5$.

Catalyst I

Catalyst I was obtained by acid activation (0.5 M $H_2SO_4$, 6 hours at 100° C.) of a commercially available montmorillonite (Terrana D from Südchemie). It had an acidity of 0.10 mmol $g^{-1}$ below $pK_a=1.5$.

Catalyst J (Comparative Example)

Catalyst J was obtained by acid activation (1 M HCl, 24 hours at 50° C.) of a commercially available vermiculite (Mikro from Ziegler). It had an acidity of 0.031 mmol $g^{-1}$ below $pK_a=1.5$.

Catalyst K (Comparative Example)

Catalyst K was a commercially available sepiolite from Sobrep. It had an acidity of 0.004 mmol $g^{-1}$ below $pK_a=1.5$.

Catalyst L (Comparative Example)

Catalyst L was a commercially available synthetic hectorite (Laponit RD from Laporte). It had no acidity below $pK_a=1.5$. The example shows that although catalysts having insufficient acidity can achieve sufficiently high conversions, the isomer ratio is worsened.

Catalyst M

Catalyst M was a commercially available sepiolite from Oxymine. It had an acidity of 0.05 mmol $g^{-1}$ below $pK_a=1.5$.

Catalyst N (Comparative Example)

Catalyst N was a commercially available hectorite (Bentone MA from Rheox). It had no acidity below $pK_a=1.5$. The example shows that although catalysts having insufficient acidity can achieve sufficiently high conversions, the isomer ratio is worsened.

Reaction to form polyamines 160 g (1.5 mol) of o-toluidine were admixed at room temperature with 7.5 g (0.25 mol) of formaldehyde (as a 37% strength aqueous solution) and the water was subsequently removed at 150° C. by means of a water separator. The resulting solution of this precondensate in toluidine was used directly for the reaction with the catalysts c).

For this purpose, in each case 40% by weight (based on the adduct of formaldehyde and two molecules of toluidine) of catalyst c) was added in powder form and the mixture was heated while stirring to 100° C. The results obtained using the various catalysts c) after different reaction times are shown in Table 1. A content of about 30% of methylenediltoluidine here corresponds to the maximum possible yield. The isomer ratio indicated gives the proportion of the 4,4' isomer relative to the 2,4' isomer.

| Catalyst c) | Running time (h) | Methyleneditoluidine [%] | Isomer ratio |
|---|---|---|---|
| A | 0.5 | 4.5 | |
| A | 1 | 7.1 | |
| A | 2 | 10.6 | |
| B | 0.5 | 29.2 | 14.6 |
| B | 1 | 29.4 | 14.0 |
| B | 2 | 28.8 | 12.5 |
| C | 0.5 | 11.4 | |
| C | 1 | 17.9 | |
| C | 2 | 24.4 | 10.6 |
| D | 0.5 | 1.7 | |
| D | 1 | 3.9 | |
| D | 2 | 6.9 | |
| E | 0.5 | 1.4 | |
| E | 1 | 3.5 | |
| E | 2 | 7.1 | |
| F | 0.5 | 29.0 | 10.6 |
| F | 1 | 29.1 | 10.4 |
| F | 2 | 29.1 | 9.4 |
| G | 0.5 | 3.7 | |
| G | 1 | 5.7 | |
| G | 2 | 10.1 | |
| H | 0.5 | 11.0 | |
| H | 1 | 18.7 | |
| H | 2 | 25.5 | |
| I | 0.5 | 29.0 | 11.1 |
| I | 1 | 29.4 | 10.1 |
| I | 2 | 29.2 | 9.1 |
| J | 0.5 | 4.4 | |
| J | 1 | 8.0 | |
| J | 2 | 13.0 | |
| K | 0.5 | 4.0 | |
| K | 1 | 7.8 | |
| K | 2 | 12.4 | |
| L | 0.5 | 16.0 | |
| L | 1 | 19.8 | |
| L | 2 | 25.9 | 6.6 |
| M | 0.5 | 17.0 | |
| M | 1 | 23.8 | |
| M | 2 | 28.0 | 10.3 |
| N | 0.5 | 7.9 | |
| N | 1 | 17.3 | |
| N | 2 | 25.4 | 6.5 |

We claim:

1. A process for preparing aromatic polyamine mixtures which contain compounds of the formula (I)

where A and B are 1,4-phenylene radicals each of which independently of one another can have from 1 to 4 substituents selected from $C_{1-20}$ alkyls and halogens, by reacting a compound of the formula (IV)

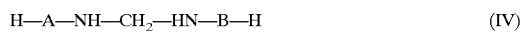

and/or a compound of the formula (V)

where A and B are substituted as defined above,
at from 20° C. to 200° C. in the presence of a heterogeneous inorganic catalyst which is selected from the group consisting of a) one or more oxides of elements of group 3 to group 10 of the Periodic Table of Elements, except vanadium, which can be acid-activated by sulfuric acid, phosphoric acid or hydrochloric acid and can thus contain sulfate, phosphate or chloride, b) a catalyst comprising a clay which is doped with at least one oxide of elements of groups 2 to 13 or the lanthanides of the Periodic Table of the Elements, carried out by impregnation or by means of ion exchange, and can be acid-activated or c) a catalyst comprising one or more silicates which can be acid-activated and have an acidity below $pK_a=1.5$ of more than 0.05 mmol/g of catalyst.

2. A process as claimed in claim 1, wherein the compound of the formulae (IV) or (V) is obtained by reacting aniline, which is unsubstituted or substituted at the aromatic ring in the o- or m-position with from 1 to 4 substituents selected from $C_{1-20}$ alkyls or halogens, with formaldehyde or formaldehyde precursors.

3. A process for preparing aromatic polyamine mixtures which contain compounds of the formula (I)

where A and B are 1,4-phenylene radicals each of which independently of one another can have from 1 to 4 substituents selected from $C_{1-20}$ alkyls and halogens,
by reacting anilines, which are unsubstituted or substituted at the aromatic ring in the o- or m-position with from 1 to 4 substituents selected from $C_{1-20}$ alkyls and halogens, with formaldehyde or formaldehyde precursors at from 20° C. to 200° C. in the presence of a heterogeneous inorganic catalyst selected from the group consisting of a) one or more oxides of elements of group 3 to group 10 of the Periodic Table of the Elements, except vanadium, which can be acid-activated by sulfuric acid, phosphoric acid or hydrochloric acid and can thus contain sulfate, phosphate or chloride, b) a catalyst comprising a clay which is doped with at least one oxide of elements of group 2 to 13 or the lanthanides of the Periodic Table of the Elements, carried out by impregnation of ion exchange, and can be acid-activated or c) a catalyst comprising one or more sheet silicates which can be acid-activated and have an acidity below $pK_a=1.5$ of more than 0.05 mmol/g of catalyst.

4. A process as claimed in claim 2, wherein the water produced in the reaction is continuously removed.

5. A process claimed in claim 3, wherein the water produced in the reaction continuously removed.

6. A process as claimed in claim 3, wherein the aromatic rings are unsubstituted at at least one o-position to the amino group and the aromatic polyamide mixtures in addition contain compounds of the formulae (II) and/or (III)

where D is a 1,2-phenylene radical and B is a 1,4-phenylene radical, which may be substituted by substituents as defined in claim 3,

   III where D and E are 1,2-phenylene radicals, which may substituted by substituents as defined in claim 3.

7. A process as claimed in claim 3, wherein the aromatic rings are unsubstituted at at least one opposition to the amino group and the aromatic polyamide mixtures in addition contain compounds of the formulae (II) and/or (Ill)

   III where D is a 1,2-phenylene radical and B is a 1,4-phenylene radical, which may be substituted by substituents as defined in claim 3,

   III where D and E are 1,2-phenylene radicals, which may be substituted by substituents as defined in claim 3.

8. A process as claimed in claim 2, wherein aniline or o-toluidine is used.

9. A process as claimed in claim 3, wherein aniline or o-toluidine is used.

10. A process as claimed in claim 1, wherein, as catalyst, use is made of a) one or more oxides of elements of group 4 to group 6 of the Periodic Table of the Elements, where the catalyst can be acid-activated by sulfuric acid, phosphoric acid or hydrochloric acid and can thus contain sulfate, phosphate or chloride or b) one or more clays which are doped with at least one oxide of elements of group 2, 3, 4, 13 or the lanthanides of the Periodic Table of the Elements can be acid-activated or c) one or more sheet silicates which can be acid-activated and are selected from the group consisting of saponites, hectorites, montmorillonites, sepiolites or attapulgites.

11. A process as claimed in claim 3, wherein, as catalyst, use is made of a) one or more oxides of elements of group 4 to group 6 of the Periodic Table of the Elements, where the catalyst can be acid-activated by sulfuric acid, phosphoric acid or hydrochloric acid and can thus contain sulfate, phosphate or chloride or b) one or more clays which are doped with at least one oxide of elements of group 2, 3, 4, 13 or the lanthanides of the Periodic Table of the Elements can be acid-activated or c) one or more sheet silicates which can be acid-activated and are selected from the group consisting of saponites, hectorites, montmorillonites, sepiolites or attapulgites.

12. A process as claimed in claim 1, wherein a) as catalyst, use is made of titanium dioxide, tungsten oxide, molybdenum oxide, zirconium dioxide or mixtures of these, where the catalyst can be acid-activated by sulfuric acid, phosphoric acid or hydrochloric acid and can thus contain sulfate, phosphate or chloride or b) the catalyst contains from 0.1 to 20% by weight, based on the total weight of the catalyst, of dopants, calculated as metal oxide of the most stable oxide after ignition at 900° C.

13. A process as claimed in claim 3, wherein a) as catalyst, use is made of titanium dioxide, tungsten oxide, molybdenum oxide, zirconium dioxide or mixtures of these, where the catalyst can be acid-activated by sulfuric acid, phosphoric acid or hydrochloric acid and can thus contain sulfate, phosphate or chloride or b) the catalyst contains from 0.1 to 20% by weight, based on the total weight of the catalyst, of dopants, calculated as metal oxide of the most stable oxide after ignition at 900° C.

14. A process as claimed in claim 1, wherein the compound of the formula (I) is formed as main product.

15. A process as claimed in claim 3, wherein the compound of the formula (I) is formed as main product.

16. A process as claimed in claim 1, wherein the reaction is carried out in the absence of a solvent.

17. A process as claimed in claim 3, wherein the reaction is carried out in the absence of a solvent.

* * * * *

UNITED STATES PATENT AND TRADEMARK OFFICE
CERTIFICATE OF CORRECTION

PATENT NO. : 6,410,789 B1
DATED : June 25, 2002
INVENTOR(S) : Becker et al.

It is certified that error appears in the above-identified patent and that said Letters Patent is hereby corrected as shown below:

<u>Column 13,</u>
Line 10, "one opposition" should be -- one o-position --.

Signed and Sealed this

Fifteenth Day of October, 2002

*Attest:*

*Attesting Officer*

JAMES E. ROGAN
*Director of the United States Patent and Trademark Office*